United States Patent
Bruce et al.

(10) Patent No.: US 8,540,634 B2
(45) Date of Patent: Sep. 24, 2013

(54) METHOD AND DEVICE FOR PRODUCING IMAGES OF HEATING TINES NEAR A TISSUE PART

(75) Inventors: Matt Bruce, Aix en Provence (FR); Thomas Gauthier, Seattle, WA (US); Hua Xiea, Ossining, NY (US); Anna T. Fernandez, Croton-on-Hudson, NY (US)

(73) Assignee: Koninklijke Philips N.V., Eindhoven (NL)

( * ) Notice: Subject to any disclaimer, the term of this patent is extended or adjusted under 35 U.S.C. 154(b) by 788 days.

(21) Appl. No.: 12/673,206

(22) PCT Filed: Jul. 30, 2008

(86) PCT No.: PCT/IB2008/053055
§ 371 (c)(1),
(2), (4) Date: Feb. 12, 2010

(87) PCT Pub. No.: WO2009/022251
PCT Pub. Date: Feb. 19, 2009

(65) Prior Publication Data
US 2011/0184286 A1 Jul. 28, 2011

Related U.S. Application Data

(60) Provisional application No. 60/955,893, filed on Aug. 15, 2007.

(51) Int. Cl.
*A61B 8/00* (2006.01)
(52) U.S. Cl.
USPC .......................................................... 600/439

(58) Field of Classification Search
USPC .................... 606/1, 27–32, 41; 600/442, 446, 600/466, 407, 443, 467, 587, 429, 439, 462, 600/463; 324/307
See application file for complete search history.

(56) References Cited

U.S. PATENT DOCUMENTS

| 7,025,767 B2 | 4/2006 | Schaefer |
| 2003/0171672 A1* | 9/2003 | Varghese et al. ............. 600/420 |

(Continued)

FOREIGN PATENT DOCUMENTS

WO 03/075771 A 9/2003

OTHER PUBLICATIONS

Varghese, Tomy, et al., "Elastographic measurement of the area and volume of thermal lesions resulting from radio frequency ablation: pathologic correlation." American Journal of Roentgenology, Sep. 2003, vol. 181, No. 3, Sep. 2003, pp. 701-707, XP002510301.

(Continued)

*Primary Examiner* — Elmer Chao

(57) ABSTRACT

A device (D1) is intended for producing images of heating tines (HT) coupled to a needle (N) positioned near a chosen tissue part of tissues located in an area of a body. This device (D1) comprises i) a means (ME) for estimating tissue thermal strains, induced by means of the heating tines (HT) into the tissue surrounding the chosen tissue part, from received ultrasound image data, and for deducing relative positions of these heating tines (HT) to the chosen tissue part from the estimated tissue thermal strains, and ii) a means (MC) for combining the received ultrasound image data with position data representative of the deduced relative positions to produce images of the area with thermal strain information showing the relative positions of the heating tines (HT) to the chosen tissue part.

5 Claims, 2 Drawing Sheets

(56) References Cited

U.S. PATENT DOCUMENTS

2003/0208197 A1 11/2003 Wood
2006/0200121 A1* 9/2006 Mowery ................. 606/41

OTHER PUBLICATIONS

Miller, N. R., et al., "Fundamental limitations of noninvasive temperature imaging by means of ultrasound echo strain estimation." Ultrasound in Medicine and Biology, New York, NY, US, vol. 28, No. 10, Oct. 1, 2002, pp. 1319-1333, XP004396856.

Souchon, R., et al., "Monitoring the formation of thermal lesions with heat-induced echo strain inmaging: A feasibility study." Ultrasound in Medicine and Biology, New York, NY, US. vol. 31, No. 2, Feb. 1, 2005, pp. 2129, XP004902246.

* cited by examiner

METHOD AND DEVICE FOR PRODUCING IMAGES OF HEATING TINES NEAR A TISSUE PART

FIELD OF THE INVENTION

The present invention relates to the production of images of an array of heating tines coupled to a needle around a chosen tissue part of tissues located in an area of a body, and to the assisted positioning of this array, notably for ablating this chosen tissue part.

One means here by "ablating" a process consisting in heating a tissue to induce cell destruction (or death). The "dead tissue" is next removed by the body for instance through its lymphatic system and then replaced by scar tissue.

BACKGROUND OF THE INVENTION

As it is known by the man skilled in the art, ablation of a chosen tissue part, such as a tumor (for instance a liver tumor (both primary and metastases) or a renal tumor or else uterine fibroids), can now be done in a minimally invasive way by an operator (generally a surgeon, a radiologist, or an interventional radiologist) by means of a remotely controllable needle coupled to an array of heating tines which can be deployed from the needle with the assistance of real time images displayed onto a screen for placement guidance.

In order to ablate a chosen tissue part, one may acquire image data in the area comprising this chosen tissue part to display real time images of this area onto a screen, then one may position the needle and deploy the heating tines near the chosen tissue part with the assistance of the displayed real time images, and finally one may heat the tissues near the chosen tissue part by means of the heating tines at a temperature which is adapted for inducing cell destruction into the chosen tissue part.

For instance, the tissue heating can be performed by a radiofrequency (RF) excitation through the heating tines. In this case, the ablation technique is called RadioFrequency Ablation (or RFA). This type of ablation method is notably described in the patent documents U.S. Pat. No. 7,025,767 and US 2003/0208197.

In case of an RFA technique the assistance (or guidance) through ultrasound (or echoes) images is widely used because it offers spatial and temporal advantages over other techniques of image acquisition such as computed tomography (or CT) and magnetic resonance imaging (or MRI).

In order for the above mentioned ablating method to be effective, the array of tines must be deployed uniformly in angle and could also possibly curve back. But, due to inhomogeneities in tissues and vessels (including in tissue and vessel stiffness), actual heating tine deployment is often not uniformly accomplished, which produces cold spots that do not allow local ablations, and/or induces flattening of heating tines, which produces a more pyramidal treatment volume instead of a desired spherical or toroidal shaped volume.

To improve the heating tine deployment it is mandatory to precisely visualize the margins of the tissue part to be ablated and the array of heating tines, and therefore the relative positions of the heating tines with respect to the tissue part to be ablated. But the visualization of the heating tines appears to be difficult, notably with a conventional B-mode ultrasound technique, due to the size of the heating tines and the brightness of the surrounding tissues (a portion of a heating tine or of a subset of heating tines can be visualized if it is well oriented relative to the ultrasound beam).

For instance, in case of an RFA method one often uses temperature or electrical impedance measurements of the tines to determine RFA efficiency and determine when RFA is complete. But, when the deployment is partly incorrect, ablation errors may occur, resulting in smaller-than-desired ablation areas and thus incomplete treatment of desired tumor-region ablation.

So, the object of this invention is to produce images of an area showing the relative positions of heating tines with respect to a chosen tissue part, for instance to improve the positioning of these heating tines, and hence to improve the efficiency of an ablation technique and to reduce the occurrence of errors.

SUMMARY OF THE INVENTION

For this purpose, it provides Method for producing images of heating tines (HT) coupled to a needle (N) positioned near a chosen tissue part of tissues located in an area of a body, the method comprising the following steps:
  receiving ultrasound image data of said area,
  estimating thermal strains, induced by means of said heating tines (HT) into the tissue surrounding said chosen tissue part, from said received ultrasound image data, and deducing from said estimated tissue thermal strains relative positions of said heating tines (HT) with respect to said chosen tissue part, and
  combining said received ultrasound image data with position data representative of said deduced relative positions, to produce images of said area showing the relative positions of said heating tines with respect to said chosen tissue part.

The image production method according to the invention may include additional characteristics considered separately or combined, and notably:
  the tissue thermal strains may correspond to localized volume expansions of the tissues and localized sound speed variations;
  one may estimate thermal strains from the received ultrasound image data. Depending on the dimension of the received ultrasound data, one may generate a two (2D) dimensional thermal strain image or three (3D) dimensional thermal strain image (or volume) from the estimated thermal strains;
  one may deduce position data of the heating tines relative to the chosen tissue part from the 2D or 3D strain image and one may overlay each image defined by received ultrasound image data with the deduced position data;
  in a variant one may deduce position data of the heating tines relative to the chosen tissue part from the 2D or 3D strain image and one may combine the data defining each image defined by received ultrasound image data with the position data to produce a modified image;
  one may estimate the tissue thermal strains from the acquired ultrasound image data by means of a technique chosen in a group comprising at least a speckle tracking technique, a Doppler-based technique, and any technique that can estimate position of the heating tines from information deduced from changes in local sound speed and/or local temperature;
  the received ultrasound image data may be 3D-ultrasound volume image data.

The invention also provides a Method for positioning heating tines (HT) coupled to a needle (N) in relation to a chosen tissue part of tissues located in an area of a body, in the method comprising the following steps:

acquiring ultrasound image data in said area in order to display real time images of said area onto a screen (SC), positioning the needle (N) and deploying the heating tines (HT) near said chosen tissue part with the assistance of said displayed real time images, pre-heating by means of said heating tines (HT) to at least one temperature adapted for inducing tissue thermal strains, estimating said tissue thermal strains from said acquired ultrasound image data and deducing relative positions of said heating tines (HT) to said chosen tissue part from said estimated tissue thermal strains, and displaying real time images of said area, showing the relative positions of said heating tines with respect to said chosen tissue part onto the screen (SC), in order to determine whether the current position of at least one of the heating tines (HT) needs to be adjusted.

It is important to notice that the imaging position (i.e. the ultrasound probe array) is not moved from the original position where the first set of images is taken. The ultrasound probe(s) must stay in the same place (held by physician, for instance) so that the imaging plane is minimally-disturbed throughout the "real-time" processing of the thermal strain and it is displayed to highlight the heating tines.

The positioning method according to the invention may include additional characteristics considered separately or combined, and notably:

the tissue thermal strains may correspond to localized volume expansions of the tissues and localized sound speed variations;

one may estimate thermal strains from the received ultrasound image data. Depending on the dimension of the acquired ultrasound data, one may generate a two (2D) dimensional thermal strain image or three (3D) dimensional thermal strain image (or volume) from the estimated thermal strains;

one may deduce position data of the heating tines relative to the chosen tissue part from the 2D or 3D strain image and one may overlay the displayed real time images with the deduced position data;

in a variant one may deduce position data of the heating tines relative to the chosen tissue part from the 2D or 3D strain image and one may combine the data defining each real time image with the position data to produce a modified real time image to be displayed onto the screen;

one may pre-heat the tissues by means of radiofrequency excitation through the heating tines;

one may pre-heat the tissues by increasing progressively their temperature from approximately 37° C. to approximately 50° C. (this pre-heating temperature is usually less than the temperatures needed to induce cell destruction);

The invention also provides a method for ablating a chosen tissue part of tissues located in an area of a body by means of heating tines (HT) coupled to a needle (N), the method comprising the following steps:

acquiring ultrasound image data in said area in order to display real time images of said area onto a screen (SC), positioning the needle and deploying the heating tines (HT) near said chosen tissue part with the assistance of said displayed real time images, pre-heating by means of said heating tines (HT) to at least one temperature adapted for inducing tissue thermal strains, estimating said tissue thermal strains from said acquired ultrasound image data and deducing from said estimated tissue thermal strains relative positions of said heating tines (HT) to said chosen tissue part, displaying real time images of said area showing the relative positions of said heating tines (HT) with respect to said chosen tissue part onto the screen (SC), in order to adjust, if necessary, the current position of at least one of the heating tines (HT) with respect to said chosen tissue part, and heating the tissues by means of said heating tines (HT) to at least one temperature for a required time allowing ablation of said chosen tissue part from said heated tissues through tissue cell destruction.

Such an ablation method may comprise anyone of the above mentioned additional characteristics of the positioning method. But, one may also heat the tissues after the fine position adjustment by increasing progressively their temperature from approximately 50° C. to approximately 90° C. to achieve tissue cell destruction (or death).

The invention also provides a computer program comprising instructions which when executed enables to carry out the methods of the inventions.

The invention further provides a Device for ablating a chosen tissue part of tissues located in an area of a body by means of heating tines (HT) coupled to a needle (N), the device comprising: means (MA) for acquiring ultrasound image data in said area and producing real time images from said acquired ultrasound image data, a screen (SC) for displaying said real time images, means (MP) for allowing an operator to position the needle (N) and to deploy the heating tines (HT) near said chosen tissue part while looking at said displayed real time images, means (MH) for causing said heating tines (HT) to heat said tissues near said chosen tissue part to at least one pre-heating temperature adapted for inducing tissue thermal strains, means (ME) for estimating said tissue thermal strains from said acquired ultrasound image data and for deducing relative positions of said heating tines (HT) to said chosen tissue part from said estimated tissue thermal strains, and means (MC) for combining said acquired ultrasound image data with position data representative of said deduced relative positions to compel said screen (SC) to display real time images of said area with thermal strain information showing the relative positions of said heating tines (HT) to said chosen tissue part, in order to allow said operator to determine if the heating tines (HT) are positioned at the desired areas and to adjust the position of at least one of said heating tines (TN).

The image production device according to the invention may include additional characteristics considered separately or combined, and notably:

its estimating means may be arranged for determining localized volume expansions of the tissues and localized sound speed variations from the received ultrasound image data and for estimating tissue thermal strains from the determined localized volume expansions and localized sound speed variations;

its estimating means may be arranged for estimating tissue thermal strains from the received ultrasound image data, and for generating a 2D or 3D thermal strain image from these estimated tissue thermal strains depending on the dimension of the received ultrasound data;

its combining means may be arranged for overlaying each image defined by received ultrasound image data with the position data (deduced by the estimation means);

the overlaid data may be 2D or 3D ultrasound images;

in a variant its combining means may be arranged for combining the data defining each image defined by received ultrasound image data with the position data (deduced by the estimation means) to produce a modified image;

its estimating means may be arranged for estimating the tissue thermal strains from the received ultrasound image data by means of a technique chosen in a group comprising at least a speckle tracking technique, a Doppler-based technique, and any technique that can estimate position of the heating tines from information deduced from changes in local sound speed and/or local temperature;

the received ultrasound image data may be 3D-ultrasound volume image data.

The invention also provides a device intended for positioning heating tines coupled to a needle in relation to a chosen tissue part of tissues located in an area of a body. This positioning device comprises:

a means for acquiring ultrasound image data in the area and producing real time images from these acquired ultrasound image data, a screen for displaying the real time images, a means for allowing an operator to position the needle and to deploy the heating tines near the chosen tissue part while looking at the displayed real time images, a means for compelling the heating tines to heat the tissues near the chosen tissue part to at least one pre-heating temperature adapted for inducing tissue thermal strains, a means for estimating the tissue thermal strains from the acquired ultrasound image data and for deducing relative positions of the heating tines to the chosen tissue part from the estimated tissue thermal strains, and a means for combining the acquired ultrasound image data with position data representative of the deduced relative positions to compel said screen to display real time images of the area with thermal strain information showing the relative positions of the heating tines to the chosen tissue part, in order to allow the operator to determine if the heating tines are positioned at the desired areas and to adjust the position of at least one of the heating tines.

The positioning device according to the invention may include additional characteristics considered separately or combined, and notably:

said estimating means (ME) is arranged for determining localized volume expansions of said tissues and localized sound speed variations from said acquired ultrasound image data and for estimating tissue thermal strains from said determined localized volume expansions and localized sound speed variations;

said estimating means (ME) is arranged for estimating tissue thermal strains from said acquired ultrasound image data, and for generating a two or three dimensional strain image from said estimated tissue thermal strains depending on the dimension of the acquired ultrasound data;

said combining means (MC) is arranged for overlaying each displayed real time image with said position data deduced by said estimation means (ME);

said combining means (MC) is arranged for combining the data defining each real time image with said position data deduced by said estimation means (ME) to produce a modified real time image to be displayed onto said screen (SC);

said means (MH) for causing said heating tines (HT) to heat said tissues near said chosen tissue part to at least one pre-heating temperature adapted for inducing tissue thermal strains is arranged for causing said heating tines (HT) to pre-heat said tissues by means of radiofrequency excitation;

said means (MH) for causing said heating tines (HT) to heat said tissues near said chosen tissue part to at least one pre-heating temperature adapted for inducing tissue thermal strains is arranged for causing said heating tines (HT) to increase progressively the temperature of said tissues from approximately 37° C. to approximately 50° C. and then perform a time pause for checking whether said position adjustment has to be carried out;

said estimating means (ME) is arranged for estimating said tissue thermal strains from said acquired ultrasound image data by means of a technique chosen in a group comprising at least a speckle tracking technique, a Doppler-based technique, and any technique that can estimate position of the heating tines (HT) from information deduced from changes in local sound speed and/or local temperature;

it further comprises control means (MO) for ordering, said means (MH) for causing said heating tines (HT) to heat said tissues near said chosen tissue part to at least one pre-heating temperature adapted for inducing tissue thermal strains, to heat said tissues near said chosen tissue part to at least one heating temperature for a required time which allows ablation of said chosen tissue part from said heated tissues through tissue cell destruction;

said means (MH) for causing said heating tines (HT) to heat said tissues near said chosen tissue part to at least one pre-heating temperature adapted for inducing tissue thermal strains is arranged for causing said heating tines (HT), after said time pause position adjustment(s), to increase progressively the temperature of said tissues from approximately 50° C. to approximately 90° C.

DESCRIPTION OF THE DRAWINGS

Other features and advantages of the invention will become apparent on examining the detailed specifications hereafter and the appended drawings, wherein.

The appended drawings may not only serve to complete the invention, but also to contribute to its definition, if need be.

DETAILED DESCRIPTION OF EMBODIMENTS

As mentioned in the introductory part, the invention aims at producing images of an area showing the relative positions of heating tines coupled to a needle relative to a chosen tissue part of a body, for instance to improve the positioning of these heating tines, and hence to improve the efficiency of an ablation technique and to reduce the occurrence of errors.

For this purpose, the invention notably proposes an image production device and an image production method.

Figure 1:
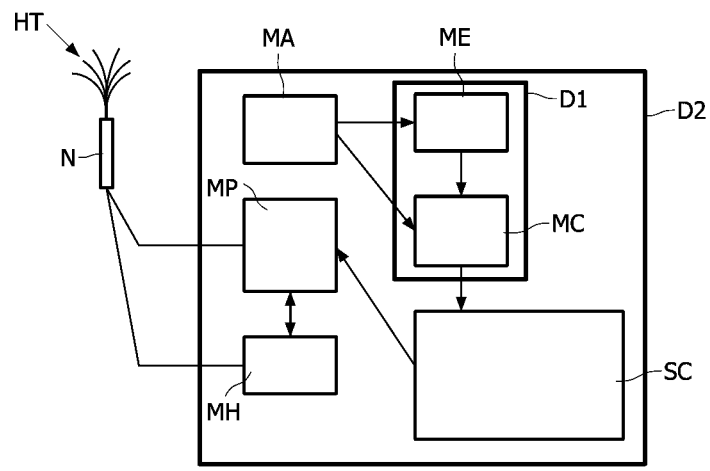
FIG. 1 schematically and functionally illustrates an example of embodiment of a positioning device according to the invention, including an image production device according to the invention, FIG. 2 schematically illustrates, in a top view, an area comprising a tissue part to be ablated and a needle coupled to an array of tines deployed around this tissue part, and FIG. 3 schematically and functionally illustrates an example of embodiment of an ablation device according to the invention, including an image production device according to the invention.
Figure 2:
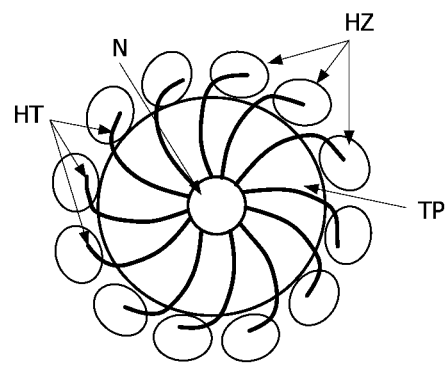

Reference is initially made to FIGS. 1 and 2 to present the image production method and an example of embodiment of an image production device D1 according to the invention. In the non limiting illustrated example the image production device D1 is part of an example of embodiment of a positioning device D2 according to the invention. But this is not mandatory.

A positioning device D2 comprises at least an array of heating tines HT coupled to a needle N, an image acquisition means MA, a screen SC, a positioning means MP, a heating module MH, an estimation module ME and a combination module MC. The estimation module ME and the combination module MC constitute the image production device D1 according to the invention.

The needle N is intended to be introduced into the body of a patient and positioned in an area which comprises a tissue part TP to be ablated, for instance a liver tumor. An operator such as a surgeon, a radiologist, or an interventional radiologist can remotely control its position by means of the positioning means MP (which is a man/machine interface well known by the man skilled in the art and therefore which will not be described hereafter).

The needle N contains the heating tines HT. Once the needle tip is placed in the desired center location of the target (i.e. the chosen tissue part to be ablated) by means of the positioning means MP, the operator can deploy or retract the heating tines HT it contains (still by means of the positioning means MP) by pushing/pulling on the needle shaft that has an inner cylinder that controls deployment (think of a syringe or biopsy needle type of device). Hence the operator controls how far the heating tines HT are deployed (usually the RF positioning (D2) or ablation (D3) device manufacturer has put marking on the needle shaft to indicate how far the "inner tube shaft" should be pushed in to form a 2 cm diameter lesion, or a 3 cm diameter lesion, for instance).

The heating tines HT are flexible electrodes whose extremities are capable of heating a tissue. Generally the positions of the heating tines HT are adjusted together. But some devices allow the operator to adjust separately the positions of every heating tine HT or of groups of heating tines.

The heating module MH is intended for compelling the heating tines HT to heat the surrounding portions of tissues on which they are respectively applied and which are located around the chosen tissue part TP to be ablated.

For instance, the tissue heating can be performed by a radiofrequency (RF) excitation through the extremities of the heating tines HT, under control of the heating module MH. One will notice that it is also possible to destruct the tissue cells by freezing them through cryo-ablation.

It is important to notice that the heating phase, which is carried out during the position adjustment of the heating tines HT around the chosen tissue part TP, is only a pre-heating phase which is adapted for inducing thermal strains into the tissues, but not for ablating the chosen tissue part TP.

When a chosen RF power is applied to the heating tines HT, the tissue zones TZ, on which their extremities are applied, are locally and rapidly heated, which produces a localized volume expansion and a sound speed variation which together define thermal strains.

For instance during the pre-heating phase the heating means MH may provide a progressively increasing RF power to the heating tines HT in order that they increase progressively the temperature of the tissue zones TZ from approximately 37° C. to approximately 50° C. This pre-heating temperature is usually less than the temperatures needed to induce cell destruction.

During this progressive increase of temperature the local sound speed C increases pseudo-linearly for most non-fat tissues. For instance, in the case of human liver tissue and human muscles the sound speed variation over temperature T (dC/dT—derivative of sound speed C over temperature T) is comprised between 0.90 m/s per degree and 1.40 m/s per degree, as described in the document of Pereira, F. R.; Machado, J. C.; Foster, F. S. "Ultrasound Characterization of Coronary Artery Wall In Vitro Using Temperature-Dependent Wave Speed", IEEE UFFC 2003, vol 11. So, if temperature rises 1 degree, the average strain (deformation) is approximately equal to 0.08%.

When the final temperature, preferably around 50° C., of the pre-heating phase is reached, a time pause occurs. As will be understood later the time pause enables to give for checking whether at least one tines needs to be adjusted. In this regard, a prompt can be displayed on the screen to inform an operator that the system is paused.

As will be described later, if the operator desires to stop the pause, he can activate the control module in this effect.

The image acquisition means MA are intended for acquiring ultrasound (or echoes) image data in the concerned area and for producing real time images from these acquired ultrasound image data. These data can be acquired by an ultrasonic probe which is placed on the skin of the patient near the concerned area by an operator.

The produced images may be of the B-mode type or contrast type, for instance. But it could be also 3D B-mode ultrasound images or Doppler images or else variations of B-mode images (for instance obtained through harmonic imaging), and more generally any type of image available on commercial ultrasound devices (or machines).

The estimation module ME is coupled to the image acquisition means MA in order to be fed with (or receive) the data defining the real time images it produces. It is intended for estimating tissue thermal strains that are induced by the pre-heating, from the ultrasound image data acquired by the image acquisition means MA (actually during the pre-heating step).

For instance, when the tissue temperature increases of 13° C. (from 37° C. to 50° C.) with an appropriate frame rate, thermal strains of about 1% (13×0.08%/degree) can be deduced from the ultrasound image data. The estimation module ME can deduce these thermal strains by implementing a speckle tracking technique or a Doppler-based technique, for instance. These techniques being well known by the man skilled in the art they will not be described hereafter.

Once the estimation module ME has estimated the tissue thermal strains, induced by the pre-heating phase around the chosen tissue part TP, it deduces the relative positions of the heating tines HT to this chosen tissue part TP from the estimated tissue thermal strains.

In order to ease the position deduction the estimation module ME may first build a 2D or 3D thermal strain image (the dimension depends on the dimension of the received ultrasound data), and then deduce the relative positions from this 2D or 3D strain image.

The combining module MC is both coupled to the acquisition means MA and the estimation module ME to be fed both with the data defining the relative positions of the heating tines HT and the acquired ultrasound image data. It is intended for combining the acquired ultrasound image data with the position data and to compel the screen SC to display real time images of the concerned area with thermal strain information which show the relative positions of the heating tines HT to the chosen tissue part, as illustrated in FIG. 2.

The combining module MC can combine the image data and the position data according to at least two different manners.

For instance, the combining module MC may overlay each real time image, produced by the image acquisition means MA and displayed onto the screen SC, with the respective representations of the heating tines HT at their respective deduced positions. In other words one displays both the ultrasound image and the thermal strain image of the heating tines HT so that the user may identify the location of the heating tines HT with respect to the target zone to ablate. This can be done by means of a so-called registration technique.

In a variant, the combining module MC may combine (or merge) the data defining each real time image (acquired by the image acquisition means MA) with the data representing the respective representations of the heating tines HT at their respective deduced positions in order to produce modified real time images. So, in this case the combining module MC provides the screen SC with the modified real time images in order it displays them sequentially. In other words ultrasound image data (for instance B-mode images) are processed to extract out the thermal strain from the heating tines HT and thus only the outline of the heating tines HT, and then one uses some additional image processing technique(s) to essentially outline the heating tines on the regular B-mode images in an overlaid image.

It is possible to display a single image on the screen SC, or side-by-side images where the right-side image is the regular B-mode image and the left-side image is the combined image, for instance.

When the operator in charge of the needle N and the heating tines HT visualizes the images displayed onto the screen SC he can determine which heating tine HT is not properly positioned and then proceed to its position adjustment before the ablation starts if needed.

It is to be noted here that, in the context of this invention, position adjustment can either mean causing a translation or a rotation of the tines.

It can further mean retracting the tines in the needle and then deploying again the tines, the needle staying in position.

This latter method can indeed enable to get all the ines positioned correctly.

The invention also proposes an ablation method and an ablation device.

Figure 3:
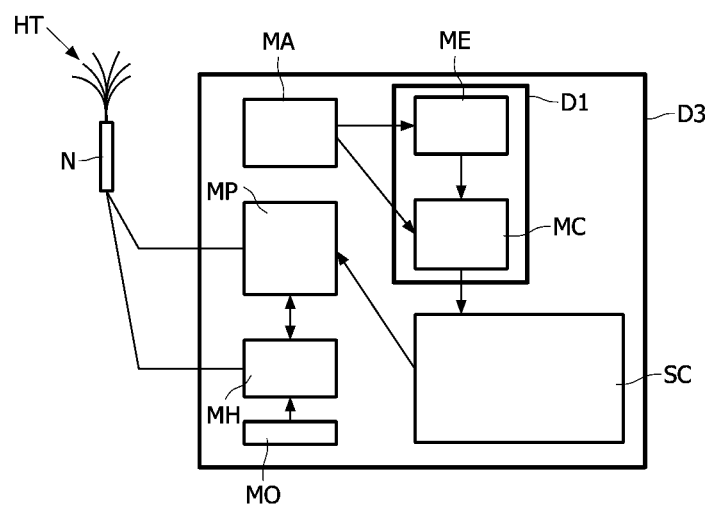

Reference is now made to FIG. 3 to present the ablation method and an example of embodiment of an ablation device D3 according to the invention.

An ablation device D3 comprises every element constituting a positioning device D3 and an additional element called control module MO. so, as illustrated in FIG. 3, it comprises at least an array of heating tines HT coupled to a needle N, an image acquisition means MA, a screen SC, a positioning means MP, a heating module MH, an estimation module ME, a combination module MC, and a control module MO.

This control module MO is activated by the operator once it has finished to adjust the positions of the heating tines HT and then wants to proceed to the ablation of the chosen tissue part TP.

Once activated, the control module MO orders to the heating module MH to heat the tissue zones TZ on which their extremities are respectively applied and which are located around the chosen tissue part TP to be ablated.

It is important to notice that this heating phase, which is carried out after the fine positioning of the heating tines HT around the chosen tissue part TP, is now adapted for ablating the chosen tissue part TP through tissue cell destruction.

For instance during this heating phase the heating means MH may provide a progressively increasing RF power to the heating tines HT in order they increase progressively the temperature of the tissue zones TZ from approximately 50° C. to approximately 90° C. to achieve tissue cell destruction (or death).

Cell death (or destruction) occurs at high temperatures and when the high temperatures are sustained over a required time (typically several minutes). For this purpose, the ablation device D3 increases the RF power to a desired peak temperature (which the operator can select) and then this peak temperature is held for several minutes. The peak temperature and the time-duration of the heating at this peak temperature are unique to the tissue to ablate. After the peak temperature is reached, there is a cool down period for the heating tines HT to reach a base temperature, then the operator retracts the heating tines HT into the needle shaft and removes the needle N from the patient. The ultimate cell destruction in the heating zone will result in dead tissue zone and the body will remove the dead cells through normal physiological behavior.

The control module MO may be also activated by the operator to start the pre-heating phase.

One will notice that the volume expansion of the tissues can still be detected by the estimation module ME during the heating phase of ablation. So, the estimation module ME may continue to produce strain images which can also be used to continually visualize the heating of the chosen tissue part TP.

Moreover, as in-vivo thermal strain measurements may be affected by cardiac motion and/or respiratory motion, for instance, patient breath-holds may be envisaged with or without general anaesthesia on board, and EKG-gated acquisitions may help to reduce influence of cardiac motion (at same position i.e. end-diastole where cardiac motion is minimum) on the ultrasound image data collected. Any other motion-compensation method may be used before final strain image processing, if necessary.

At least the estimation module ME, combination module MC and control module MO may be realized with software modules or a combination of software and hardware modules.

While the invention has been illustrated and described in detail in the drawings and foregoing description, such illustration and description are to be considered illustrative or exemplary and not restrictive; the invention is not limited to the disclosed embodiments.

In particular, other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for ablating a chosen tissue part of tissues located in an area of a body by means of heating tines coupled to a needle, the method comprising the following steps:
   positioning the needle and deploying the heating tines in said chosen tissue part,
   pre-heating the chosen tissue part by means of said heating tines to one temperature adapted for inducing localized volume expansion,
   acquiring ultrasound image data from the pre-heated tissue which indicate the effect of the localized volume expansion,
   estimating tissue thermal strains from said acquired ultrasound image data and deducing from said estimated tissue thermal strains relative positions of said heating tines to said chosen tissue part,
   displaying real time images of said area showing the relative positions of said heating tines with respect to said chosen tissue part onto a screen;
   determining whether to adjust the current position of at least one of the heating tines with respect to said chosen tissue part, and
   based on said determining, heating the tissues by means of said heating tines to a higher temperature than the one temperature for a required time allowing ablation of said chosen tissue part from said heated tissues through tissue cell destruction.

2. The method according to claim 1, wherein one pre-heats said tissues by means of radiofrequency excitation through said heating tines.

3. The method according to claim 1, wherein pre-heating further comprises increasing theif temperature of the chosen tissue part from approximately 37° C. to approximately 50° C.

4. The method according to claim 1, wherein one estimates said tissue thermal strains from said acquired ultrasound image data by means of a technique chosen in a group comprising at least a speckle tracking technique, a Doppler-based technique, and any technique that can estimate position of the heating tines from information deduced from changes in local sound speed and/or local temperature.

5. The method according to claim 1, wherein heating the tissues further comprises increasing their temperature from approximately 50° C. to approximately 90° C. to achieve tissue cell destruction.

* * * * *